(12) United States Patent
Pauley et al.

(10) Patent No.: US 7,982,089 B2
(45) Date of Patent: Jul. 19, 2011

(54) METHODS OF LUBRICATING A TAMPON AND A TAMPON LUBRICATED THEREBY

(75) Inventors: Suzanne Pauley, Dover, DE (US); Jacqueline Davis, Hackensack, NJ (US); Dane R. Jackson, Bloomingdale, NJ (US)

(73) Assignee: Playtex Products, Inc., Westport, CT (US)

( * ) Notice: Subject to any disclaimer, the term of this patent is extended or adjusted under 35 U.S.C. 154(b) by 362 days.

(21) Appl. No.: 10/754,651

(22) Filed: Jan. 9, 2004

(65) Prior Publication Data
US 2004/0153024 A1 Aug. 5, 2004

Related U.S. Application Data

(63) Continuation of application No. 09/716,083, filed on Nov. 17, 2000, now Pat. No. 6,746,418.

(51) Int. Cl.
*A61F 13/00* (2006.01)
(52) U.S. Cl. ........... 604/363; 604/385.18; 604/904; 604/12
(58) Field of Classification Search ......... 604/385.18, 604/904, 11–18, 363
See application file for complete search history.

(56) References Cited

U.S. PATENT DOCUMENTS

| | | | |
|---|---|---|---|
| 3,058,469 A | 10/1962 | Crockford | 128/285 |
| 3,139,886 A | 7/1964 | Tallman et al. | 128/263 |
| 3,335,726 A | 8/1967 | Maranto | 128/270 |
| 3,358,686 A | 12/1967 | Asaka | 128/263 |
| 3,390,671 A | 7/1968 | Hildebrand | 128/263 |
| 3,464,413 A | 9/1969 | Goldfarb et al. | 424/447 |
| 3,490,454 A | 1/1970 | Goldfarb et al. | 128/285 |
| 3,585,998 A | 6/1971 | Hayford et al. | 604/359 |
| 3,674,029 A | 7/1972 | Bates et al. | 128/285 |
| 3,821,350 A | 6/1974 | Suchane | 264/257 |
| 3,911,501 A | 10/1975 | Seltzer | 2/163 |
| 4,026,292 A | 5/1977 | Hutchins et al. | 128/285 |
| 4,056,103 A | 11/1977 | Kaczmarzyk et al. | 128/285 |
| 4,312,348 A | 1/1982 | Friese | 128/263 |
| 4,421,504 A | 12/1983 | Kline | 604/12 |

(Continued)

FOREIGN PATENT DOCUMENTS

CA 1228039 4/1971

(Continued)

OTHER PUBLICATIONS

European Search Report Dated Sep. 13, 2004.

(Continued)

*Primary Examiner* — Lynne Anderson
(74) *Attorney, Agent, or Firm* — Ohlandt, Greeley, Ruggiero & Perle, L.L.P.

(57) ABSTRACT

There is provided a tampon pledget or tampon applicator that is covered by a wrapper having microcapsules thereon. Alternatively, the microcapsules may simply be disposed on the tampon pledget or tampon applicator. The microcapsules may contain a lubricant or a fragrance or a combination of both. The microcapsules may be ruptured prior to inserting the tampon pledget or tampon applicator and the resultant free-flowing lubricant and/or fragrance is spread on the tampon pledget, tampon applicator, or a combination thereof. The lubricant increases the ease and comfort of inserting and positioning the tampon pledget or tampon applicator. The amount of lubricant desired may be controlled by varying the pressure applied to the microcapsules. Thus, the number of microcapsules ruptured can be controlled by varying the pressure applied.

13 Claims, 1 Drawing Sheet

U.S. PATENT DOCUMENTS

| | | | | |
|---|---|---|---|---|
| 4,428,747 | A | | 1/1984 | Friese et al. .................... 604/12 |
| 4,690,671 | A | | 9/1987 | Coleman et al. ................ 604/12 |
| 4,826,497 | A | | 5/1989 | Marcus et al. ................. 604/359 |
| 4,878,775 | A | * | 11/1989 | Norbury et al. ............... 401/132 |
| 5,413,747 | A | | 5/1995 | Akers et al. .................... 264/211 |
| 5,533,990 | A | | 7/1996 | Yeo ................................ 604/363 |
| 6,040,111 | A | * | 3/2000 | Karasawa et al. .......... 430/270.1 |
| 6,066,673 | A | | 5/2000 | McIver et al. .................. 514/634 |
| 6,746,418 | B1 | * | 6/2004 | Pauley et al. .................... 604/12 |

FOREIGN PATENT DOCUMENTS

| | | |
|---|---|---|
| CA | 2203949 A | 11/1988 |
| JP | 49-042976 | 11/1974 |
| JP | 57-500051 | 1/1982 |
| JP | 63-192446 | 8/1988 |
| JP | 03-259986 | 11/1991 |
| JP | 2000-080567 | 3/2000 |
| JP | 2000-513627 | 10/2000 |
| WO | WO 9526207 | 10/1995 |
| WO | WO 9953880 | 10/1999 |

OTHER PUBLICATIONS

English translation of Notification of Reasons for Rejection from corresponding Japanese Application No. 2002-542797 dated Oct. 26, 2007.

English translation of Notification of Reasons for Rejection from corresponding Japanese Application No. 2002-542797 dated May 7, 2008.

International Search Report from corresponding PCT Application No. PCT/US01/43516 dated May 31, 2002.

International Preliminary Examination Report from corresponding PCT Application No. PCT/US01/43516 dated May 7, 2003.

Written Opinion from corresponding PCT Application No. PCT/US01/43516 dated Dec. 2, 2002.

Office Action from corresponding Canadian Application No. 2,429,499 dated Jul. 7, 2008.

Office Action from corresponding Canadian Application No. 2,429,499 dated Mar. 11, 2009.

English translation of Official Notice of Preliminary Rejection from corresponding Korean Application No. 2007-7008259 dated May 11, 2007.

English translation of Official Notice of Preliminary Rejection from corresponding Korean Application No. 2007-7008257 dated May 9, 2007.

English translation of Official Notice of Preliminary Rejection from corresponding Korean Application No. 10-2007-7008258 dated Nov. 27, 2007.

English translation of Official Notice of Preliminary Rejection from corresponding Korean Application No. 2007-7008258 dated May 9, 2007.

European Examination Report from corresponding European (GB) Application No. 01996708.2 dated Dec. 20, 2004.

European Examination Report from corresponding European (GB) Application No. 01996708.2 dated Dec. 15, 2005.

English translation of Official Notice of Preliminary Rejection from corresponding Korean Application No. 2003-7006709 dated Feb. 12, 2007.

English translation of Official Notice of Preliminary Rejection from corresponding Korean Application No. 2003-7006709 dated Aug. 29, 2007.

* cited by examiner

METHODS OF LUBRICATING A TAMPON AND A TAMPON LUBRICATED THEREBY

CROSS REFERENCE TO RELATED APPLICATIONS

The present application is a Continuation of U.S. patent application Ser. No. 09/716,083 filed on Nov. 17, 2000 now U.S. Pat. No. 6,746,418.

BACKGROUND OF THE INVENTION

1. Field of the Invention

The present invention relates to methods of lubricating tampon pledgets and tampon applicators. More particularly, the present invention relates to consumer activated methods of lubricating tampon pledgets and tampon applicators for comfort and ease of insertion. The present invention also includes consumer activated methods of lubricating and fragrancing tampon pledgets and tampon applicators.

2. Description of the Prior Art

Typically, a woman will insert and position a catamenial tampon pledget using a cardboard or plastic applicator tube. However, during times of light menstrual flow or when there is a lack of vaginal moisture, insertion of a tampon pledget or tampon applicator can be very uncomfortable.

Tampon pledgets and tampon applicators have been coated with one or more lubricants to make insertion and positioning more comfortable. However, tampon pledgets and tampon applicators that have been coated with lubricant may absorb the lubricant over time and, thus, the lubricant is lost. The lubricant may also simply evaporate or dry out.

On the other hand, the lubricant may be held separately from the tampon pledget or tampon applicator until the moment that the tampon is inserted. However, women may not always be receptive to a product that obligates them to use an awkward, time consuming second step every time they insert a lubricant tampon pledget or lubricant tampon applicator.

In light of the foregoing, there is a need for an easy-to-use, convenient tampon pledget or tampon applicator having lubrication that may be used on an as needed basis.

Microencapsulation is used for a variety of personal care applications ranging from product samples found in print magazines to special additives in laundry detergents. Technology currently permits the encapsulation of both water-soluble and water-insoluble material, which includes a wide range of lubricants, such as mineral oil. Typically, microcapsules are made using silica or cellulose. The contents of the microcapsules are released at a selected time, either by pressure or by dissolving the capsule wall with a solvent.

SUMMARY OF THE INVENTION

It is an object of the present invention to provide a tampon pledget or tampon applicator that may be easily lubricated by the user.

It is also an object of the present invention to provide such a tampon pledget or tampon applicator in which the amount of the lubricant may be selectively applied by the user.

It is another object of the present invention to provide such a tampon pledget or tampon applicator in which the lubricant may be applied without the user actually touching the lubricant.

It is still another object of the present invention to provide such a tampon pledget or tampon applicator in which the lubricant may be selectively applied through the use of one or more microencapsulated lubricants.

It is a further object of the present invention to provide a wrapper for a tampon pledget and/or a tampon applicator in which one or more microcapsules having lubricant therein is positioned on the interior surface of the wrapper.

It is still a further object of the present invention to provide such a tampon pledget or tampon applicator and/or a wrapper for same in which a fragrance may be selectively applied through the use of one or more microencapsulated fragrances.

Accordingly, there is provided a tampon pledget or tampon applicator that is covered by a wrapper having microcapsules thereon. Alternatively, the microcapsules may simply be disposed on the tampon pledget or tampon applicator. The microcapsules may contain a lubricant or a fragrance or a combination of both. The microcapsules may be ruptured prior to inserting the tampon pledget or tampon applicator and the resultant free-flowing lubricant and/or fragrance is spread on the tampon pledget, tampon applicator, or a combination thereof. The lubricant increases the ease and comfort of inserting and positioning the tampon pledget or tampon applicator. The amount of lubricant desired may be controlled by varying the pressure applied to the microcapsules. Thus, the number of microcapsules ruptured can be controlled by varying the pressure applied.

Overall, this allows the consumer to apply as much lubricant and/or fragrance as desired without having to actually touch the lubricant or fragrance itself. Thus, no mess is created and no subsequent clean up is required. The lubricant provides for comfort, as well as, ease of insertion of the tampon pledget and/or tampon applicator.

DETAILED DESCRIPTION OF THE INVENTION

As used herein, the term "tampon pledget" also incorporates other catamenial devices, absorbent pledgets, and any article or device inserted into a body cavity for the purpose of absorbing fluids therein.

As used herein, the term "tampon applicator" incorporates any article or device inserted into a body cavity for the purpose of delivering a "tampon pledget".

As used herein, the term "tampon" incorporates both the "tampon pledget" and "tampon applicator".

Figure 1:
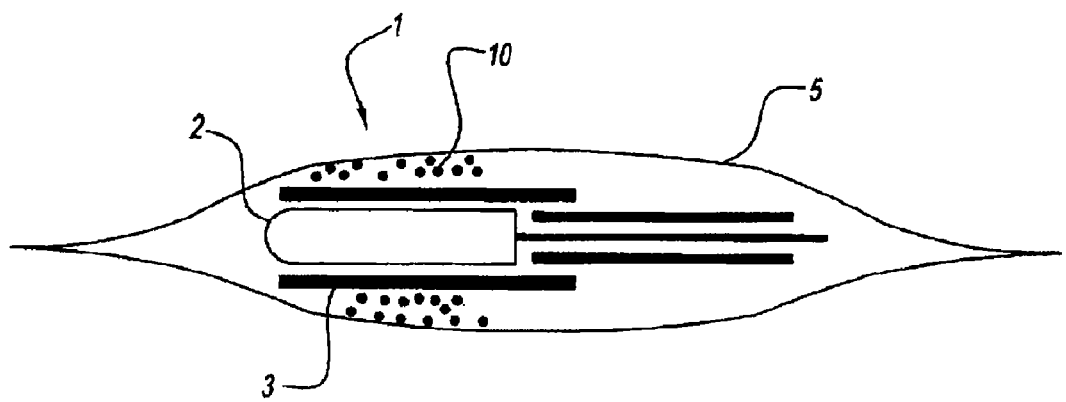
FIG. 1 is a cross-sectional view of a wrapped tampon according to the present invention.

Referring to the figures and, particularly, FIG. 1, there is provided a wrapped tampon according to the present invention, which is represented by reference numeral 1. Wrapped tampon 1 includes a tampon pledget 2, a wrapper 5, and optionally, a tampon applicator 3. One or more microcapsules 10 are affixed to any one or all of the tampon pledget 2, the wrapper 5, and/or the tampon applicator 3. The microcapsules can be affixed onto a surface of the tampon pledget 2, tampon applicator 3 or wrapper 5. Microcapsules 10 may be ruptured prior to inserting the tampon pledget 2 and/or the applicator 3 into the vagina in order to release the contents of the microcapsules onto the tampon pledget and/or the tampon applicator.

The microcapsules can contain a lubricant and/or a fragrance. When many microcapsules are used, some microcapsules may contain a lubricant, and other microcapsules may contain a fragrance. However, it is preferred that a majority of the microcapsules applied to a surface have a lubricant therein. It is also preferred that the microcapsules or any portion of the microcapsules may have both a lubricant and a fragrance.

When using a digital (non-applicator) tampon, the microcapsules 10 may be ruptured prior to inserting the tampon pledget 2 into the vagina in order to lubricate the tampon pledget. When using an applicator tampon, the microcapsules 10 may be ruptured prior to inserting the tampon pledget 2 and tampon applicator 3 into the vagina in order to lubricate the tampon applicator and possibly also a portion of the tampon pledget, depending on the configuration of the applicator tip.

Wrapped tampon 1 may be made of any material known in the art to be suitable for insertion into the body and/or the absorption of bodily fluids. Typically, tampon pledget 2 may be made of a fibrous material, such as cotton and rayon. If a tampon applicator 3 is used to insert tampon pledget 2, the tampon applicator may be made of paper, cardboard, plastic, or any other suitable material.

Wrapper 5 is preferably a flexible or semi-flexible material. It is substantially fluid impermeable, usually resistant to water vapor transmission, and will withstand normal handling without rupturing. Materials suitable for producing wrapper 5 include, without limitation, polypropylene, polyethylene, polyester, cellophane, polyvinylidene chloride, wax coated paper, film coated paper, treated paper, or combinations thereof.

Each microcapsule 10 is essentially spherical in shape and has a diameter preferably from about 500 micrometers ($\mu$m) to about 800 $\mu$m. Below about 500 $\mu$m, research has indicated that consumers or users do not perceive an adequate amount of lubrication from the microcapsules. Above about 800 $\mu$m, the microcapsules become increasingly difficult to process.

The lubricant enclosed in each microcapsule 10 may be any known in the art, such as, for example, mineral oil, vegetable oil, silicone oil, water, propylene glycol, polyglyceryl methacrylate, glyceryl laurate, polysorbate, or mixtures thereof. It is understood that in processing the plurality of microcapsules, one or more microcapsules may, in fact, inadvertently not contain lubricant. Thus, the present invention provides for a plurality of microcapsules in which a majority, but possibly not all, or a substantial number of microcapsules include lubricant therein. A preferred lubricant is medical grade mineral oil, with a preferred final lubricant weight, in each microcapsule, of about 40 milligrams (mg). The preferred lubricant weight range varies, as it is dependent on the lubricant used.

Effective lubrication of tampon 1 is achieved by securing microcapsules 10 to either tampon pledget 2, tampon applicator 3, wrapper 5, or a combination thereof. Preferably, microcapsules 10 are secured either indirectly or preferably directly to an inner surface 8 of wrapper 5.

Microcapsules 10 may be secured on inner surface 8 without a viable risk that the microcapsules 10 will unintentionally rupture and, thus, be absorbed by the tampon pledget 2 and/or the tampon applicator 3, or the wrapper 5, or break down over time.

Additionally, a fragrance may also be added to the microcapsules 10 either in conjunction with the lubricant or by itself. Preferably, the fragrance is mixed directly into the lubricant and acts as a signal for the activation of the lubricant when the microcapsules 10 are ruptured. Alternatively, the fragrance may be contained in separate microcapsules 10 that may be interspersed with the microcapsules 10 having only lubricant therein.

The fragrances that can be used are any that will not adversely effect the efficacy of the lubricant and may be otherwise used in a body cavity.

Figure 2:
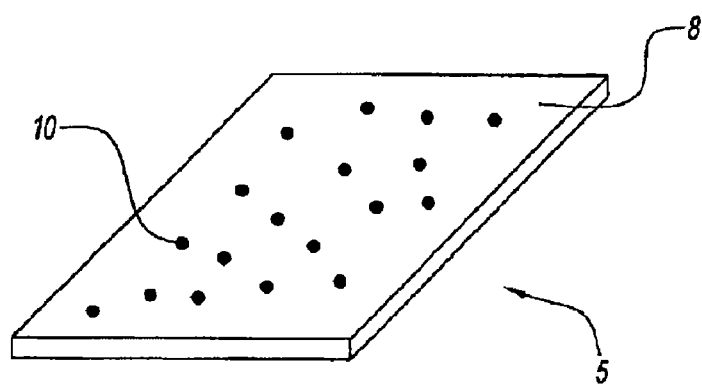
FIG. 2 is a perspective detail view of a portion of a wrapper for the tampon of FIG. 1.

As shown in FIG. 2, microcapsules 10 may be affixed to inner surface 8 of wrapper 5. Securing or affixing the microcapsules 10 to the tampon pledget 2, the tampon applicator 3, or the wrapper 5, may be achieved through any method known in the art. However, the microcapsules 10 are preferably applied by a process known as "printing". As such, microcapsules 10 are adhered using a binder material. The binder material may be any suitable material, such as methylcellulose, polyvinyl alcohol, acrylic, starch, or mixtures thereof. More preferably, the binder material is manufactured by Dow Chemical Company, Midland, Michigan and sold under the tradename Methocel. Also, the microcapsules may be applied by coating or spraying.

With the microcapsules 10 secured to the inner surface 8 of wrapper 5, when the microcapsules are ruptured, the lubricant (and/or fragrance depending on the contents of the microcapsule) is distributed over the exterior of tampon pledget 2 when using a digital tampon. When using an applicator tampon, the lubricant is distributed over the exterior of the applicator barrel (not the plunger) and possibly the insertion end or tip of the tampon pledget depending on the configuration of the applicator tip.

Wrapped tampon 1 made according to the present invention may be used as follows. In one alternative, a woman may open the wrapper 5 at approximately the midpoint and simply discard the entire wrapper. However, if the woman chooses to apply the lubricant, she leaves a portion of the wrapper over the insertion end of tampon 1, while discarding the other portion. By applying pressure to the remaining portion of wrapper 5 and simultaneously twisting the wrapper, the microcapsules secured to the inner surface of the wrapper are ruptured and the resulting free-flowing lubricant is spread on the tampon pledget, the insertion end of the tampon applicator, or both. The woman controls the amount of lubricant she requires by varying the pressure and simultaneous twisting force applied to the wrapper 5; thus controlling the amount of microcapsules ruptured. In another embodiment in which the microcapsules are positioned on the surface of the tampon applicator 3 (or the tampon pledget 2 for a digital tampon), the woman uses a portion of the wrapper like a tourniquet to squeeze and rupture the number of microcapsules desired.

Thus, the user may control the amount of lubricant desired by varying the pressure applied to the plurality of microcapsules. This, in turn, controls the number of microcapsules ruptured and results in the desired amount of lubricant being released from the microcapsules. The free-flowing lubricant from the ruptured microcapsules provides for comfort and ease of insertion of the tampon pledget and/or tampon applicator.

The present invention having been described with particular reference to the preferred forms thereof, it will be obvious that various changes and modifications may be made herein without departing from the spirit and scope of the invention as defined in the appended claims.

Wherefore we claim:

1. A tampon pledget comprising: an exterior surface, said exterior surface having a plurality of microcapsules thereon, a substantial number of said plurality of microcapsules having a lubricant as an only ingredient therein and a remainder of said plurality of microcapsules absent lubricant, wherein said plurality of microcapsules may be ruptured, as desired, for the purpose of spreading said lubricant on said exterior surface, wherein said plurality of microcapsules are on said exterior surface by a binding material, wherein each of said plurality of microcapsules range in size from 500 µm to 800 µm, and wherein said lubricant has a weight of about 40 mg per microcapsule.

2. The tampon pledget according to claim 1, wherein said lubricant is selected from the group consisting of: mineral oil, vegetable oil, silicone oil, water, propylene glycol, polyglyceryl methacrylate, glyceryl laurate, polysorbate, and any mixture thereof.

3. The tampon pledget according to claim 1, wherein said remainder of said plurality of microcapsules has fragrance therein.

4. The tampon pledget according to claim 1, wherein said exterior surface has said remainder of said plurality of microcapsules with fragrance therein, said remainder of said plurality of microcapsules being interspersed with said substantial number of said plurality of microcapsules having lubricant therein.

5. A method of lubricating a tampon comprising the steps of:
   providing a plurality of microcapsules that are adhered to an exterior surface of a tampon applicator, said plurality of microcapsules having a substantial number thereof with a lubricant therein and a remainder of said plurality of microcapsules without said lubricant therein; and
   rupturing said substantial number of said plurality of microcapsules for the purpose of spreading said lubricant onto a tampon pledget, said tampon applicator, or combination thereof.

6. The method of claim 5, further comprising varying the pressure exerted on said substantial number of said plurality of microcapsules to control the number of ruptured microcapsules and, thus, the amount of said lubricant desired.

7. The method of claim 6, wherein the pressure exerted on said substantial number of said plurality of microcapsules is applied by a portion of a wrapper over an insertion end of the tampon.

8. The method of claim 5, wherein said remainder of said plurality of microcapsules have fragrance therein.

9. The method of claim 5, wherein said rupturing one or more of said plurality of microcapsules comprises rupturing one or more of said substantial number of said plurality of microcapsules to spread said lubricant onto said tampon pledget.

10. The method of claim 5, wherein said rupturing comprises using a portion of a wrapper like a tourniquet to squeeze and rupture a number of said plurality of microcapsules.

11. The method of claim 5, wherein each of said plurality of microcapsules range in size from about 500 µm to about 800 µm.

12. A method of lubricating a tampon comprising the steps of:
   providing a plurality of microcapsules on an interior surface of a wrapper covering said tampon, said plurality of microcapsules having a substantial number thereof with a lubricant therein and a remainder of said plurality of microcapsules without said lubricant therein;
   opening said wrapper at about a midpoint of said wrapper and leaving a portion of said wrapper over an insertion end of said tampon and discarding another portion of said wrapper; and
   rupturing said substantial number of said plurality of microcapsules that comprises applying pressure to said portion of said wrapper over said insertion end of said tampon and simultaneously twisting said wrapper so that said substantial number of said plurality of microcapsules adhered thereto are ruptured resulting in free-flowing lubricant that is spread onto said tampon pledget, said tampon applicator, or combination thereof.

13. The method of claim 12, further comprising varying said pressure and said simultaneous twisting force applied to said wrapper to control an amount of said plurality of microcapsules ruptured.

\* \* \* \* \*